(12) United States Patent
Feng et al.

(10) Patent No.: US 11,354,831 B2
(45) Date of Patent: Jun. 7, 2022

(54) IMAGE RECONSTRUCTION USING TRACER AND VARIOUS PARAMETERS

(71) Applicant: UIH AMERICA, INC., Houston, TX (US)

(72) Inventors: Tao Feng, Houston, TX (US); Yizhang Zhao, Shanghai (CN)

(73) Assignee: UIH AMERICA, INC., Houston, TX (US)

( * ) Notice: Subject to any disclaimer, the term of this patent is extended or adjusted under 35 U.S.C. 154(b) by 66 days.

(21) Appl. No.: 16/658,011

(22) Filed: Oct. 18, 2019

(65) Prior Publication Data
US 2021/0118202 A1     Apr. 22, 2021

(51) Int. Cl.
G06T 11/00     (2006.01)
G06T 7/00      (2017.01)
A61B 6/00      (2006.01)

(52) U.S. Cl.
CPC .......... *G06T 11/006* (2013.01); *A61B 6/4057* (2013.01); *G06T 7/0012* (2013.01); *G06T 11/008* (2013.01); *G06T 2207/10104* (2013.01); *G06T 2207/10108* (2013.01); *G06T 2207/30104* (2013.01); *G06T 2211/424* (2013.01)

(58) Field of Classification Search
None
See application file for complete search history.

(56) References Cited

U.S. PATENT DOCUMENTS

| | | | |
|---|---|---|---|
| 9,436,989 B2 * | 9/2016 | Uber, III | A61B 6/5288 |
| 2010/0049022 A1 * | 2/2010 | Parris | A61B 5/14532 |
| | | | 600/347 |
| 2014/0151563 A1 * | 6/2014 | Rousso | G01T 1/161 |
| | | | 250/362 |

FOREIGN PATENT DOCUMENTS

| | | | | |
|---|---|---|---|---|
| CN | 106510744 A | * | 3/2017 | |
| CN | 110215224 A | | 9/2019 | |
| JP | 2006326078 A | * | 12/2006 | ............. A61B 6/507 |
| WO | WO-2015153946 A1 | * | 10/2015 | ........... A61B 5/7207 |

OTHER PUBLICATIONS

S. Sourbron, "A Tracer-Kinetic Field Theory for Medical Imaging," in IEEE Transactions on Medical Imaging, vol. 33, No. 4, pp. 935-946, Apr. 2014, doi: 10.1109/TMI.2014.2300450. (Year: 2014).*
Machine translation of CN-106510744-A (Year: 2016).*
Machine translation of JP-2006326078-A (Year: 2006).*

* cited by examiner

*Primary Examiner* — Vu Le
*Assistant Examiner* — Courtney Joan Nelson
(74) *Attorney, Agent, or Firm* — Metis IP LLC

(57) ABSTRACT

Systems and methods for image reconstruction are provided. The methods may include obtaining a first image sequence of a subject and obtaining an initial input function that relates to a concentration of an agent in blood vessels of the subject with respect to time. The first image sequence may include one or more first images generated based on a first portion of scan data of the subject. The methods may further include, for each of a plurality of pixels in the one or more first images, determining at least one correction parameter associated with the pixel and determining, based on the initial input function and the at least one correction parameter, a target input function The methods may further include generating one or more target image sequences related to one or more dynamic parameters based at least in part on a plurality of target input functions.

18 Claims, 8 Drawing Sheets

600

| Determining, based on the one or more first images in the first image sequence, an output function that indicates a concentration of the agent in at least a part of a tissue of the subject | ～ 602 |

↓

| Determining, using a first kinetic model, a relationship among the set of first dynamic parameters associated with the subject, the initial input function, the at least one correction parameter, and the output function | ～ 604 |

↓

| Determining the at least one correction parameter based on the relationship, the initial input function, and the output function | ～ 606 |

| Obtaining a second image sequence based on a second portion of the scan data, the second image sequence including one or more second images | ∿ 702 |

↓

| Generating at least one target image sequence corresponding to at least one second dynamic parameter based on a second kinetic model, the second image sequence, and the plurality of target input functions associated with the plurality of pixels in the one or more first images | ∿ 704 |

┌─────────────────────────────────────────────┐
│ Determining an estimation function for determining at least │
│ one second dynamic parameter based on a projection │ ～ 802
│ model, a second kinetic model, and the scan data │
└─────────────────────────────────────────────┘
                    ↓
┌─────────────────────────────────────────────┐
│ Determining an iterative equation for determining the at │
│ least one second dynamic parameter based on the │ ～ 804
│ estimation function │
└─────────────────────────────────────────────┘
                    ↓
┌─────────────────────────────────────────────┐
│ Generating at least one target image sequence │ ～ 806
│ corresponding to the at least one second dynamic │
│ parameter by performing an iterative operation based on the │
│ iterative equation │
└─────────────────────────────────────────────┘

FIG. 8

IMAGE RECONSTRUCTION USING TRACER AND VARIOUS PARAMETERS

TECHNICAL FIELD

The present disclosure generally relates to image processing, and more particularly, relates to systems and methods for reconstructing parametric images.

BACKGROUND

Positron emission tomography (PET) technology has been widely used for clinical examination and medical diagnosis. A radioactive tracer is usually administered to a patient before a PET scan is performed on a region of interest (ROI) of the patient. The PET system can detect radiation emitted by the radioactive tracer and reconstruct parametric images corresponding to one or more dynamic parameters associated with biological activities in the ROI. The parametric images may be used for the evaluation of the physiology (functionality) and/or anatomy (structure) of an organ and/or tissue in the ROI. For determining the one or more dynamic parameters, the same input function that indicates the concentration of the radioactive tracer in the blood or plasma is often applied to various parts of the body. A single input function does not consider effects of factors such as inhomogeneous velocity of the blood in different blood vessels, and a distance between a blood sampling site and a specific organ or tissue in the ROI. Therefore, it is desired to develop systems and methods for determining more accurate input functions, and thus generating more accurate parametric images based on the actual input functions.

SUMMARY

According to an aspect of the present disclosure, a system for image reconstruction is provided. The system may include at least one non-transitory storage medium including a set of instructions and at least one processor in communication with the at least one non-transitory storage medium. When executing the set of instructions, the at least one processor may be configured to cause the system to perform operations including obtaining a first image sequence of a subject and obtaining an initial input function that relates to a concentration of an agent in blood vessels of the subject with respect to time. The first image sequence may include one or more first images generated based on a first portion of scan data of a scan of the subject. The agent may be administered to the subject before the scan. For each of a plurality of pixels in the one or more first images, the at least one processor may be configured to cause the system to perform operations including determining at least one correction parameter associated with the pixel and determining, based on the initial input function and the at least one correction parameter, a target input function associated with the pixel. The at least one processor may be further configured to cause the system to perform operations including generating one or more target image sequences based at least in part on a plurality of target input functions associated with the plurality of pixels in the one or more first images. The one or more target image sequences may relate to one or more dynamic parameters associated with the subject, respectively.

In some embodiments, the at least one correction parameter may include at least one of a first parameter associated with a dispersion effect caused by blood circulation, or a second parameter associated with a time delay effect caused by blood circulation.

In some embodiments, the agent may include a radioactive tracer.

In some embodiments, the one or more dynamic parameters include a set of first dynamic parameters, and to determine the at least one correction parameter associated with the pixel, the at least one processor may be configured to cause the system to perform operations including determining, based on the one or more first images in the first image sequence, an output function that indicates a concentration of the agent in at least a part of a tissue of the subject. The at least one processor may be further configured to cause the system to perform operations including determining, using a first kinetic model, a relationship among the set of first dynamic parameters associated with the subject, the initial input function, the at least one correction parameter, and the output function. The at least one processor may be further configured to cause the system to perform operations including determining the at least one correction parameter based on the relationship, the initial input function, and the output function.

In some embodiments, the first kinetic model may be a one-tissue compartment model.

In some embodiments, to determine the at least one correction parameter associated with the initial input function, the at least one processor may be further configured to cause the system to perform operations including determining the at least one correction parameter based further on a preset condition associated with one or more physiological properties of the subject.

In some embodiments, to generate the one or more target image sequences, the at least one processor may be further configured to cause the system to perform operations including generating, based on the relationship among the set of first dynamic parameters, at least one of the one or more target image sequences corresponding to at least one of the set of first dynamic parameters.

In some embodiments, the one or more dynamic parameters may include a set of second dynamic parameters, and to generate the one or more target image sequences, the at least one processor may be configured to cause the system to perform operations including obtaining a second image sequence generated based on a second portion of the scan data and generating at least one of the one or more target image sequences corresponding to at least one second dynamic parameter based on a second kinetic model, the second image sequence, and the plurality of target input functions associated with the plurality of pixels in the one or more first images The second image sequence may include one or more second images.

In some embodiments, the second portion of the scan data may at least partially overlap the first portion of the scan data.

In some embodiments, the second portion of the scan data may include the first portion of the scan data.

In some embodiments, to generate the one or more target image sequences, the at least one processor may be configured to cause the system to perform operations including generating at least one of the one or more target image sequences corresponding to at least one second dynamic parameter by performing an iterative operation based on a projection model, a second kinetic model, and the scan data.

In some embodiments, the iterative operation may include a maximum likelihood estimation operation.

According to another aspect of the present disclosure, a method for image reconstruction is provided. The method may be implemented on a computing device having at least one processor and at least one non-transitory storage medium. The method may include obtaining a first image sequence of a subject and obtaining an initial input function that relates to a concentration of an agent in blood vessels of the subject with respect to time. The first image sequence may include one or more first images generated based on a first portion of scan data of a scan of the subject. The agent may be administered to the subject before the scan. The method may further include, for each of a plurality of pixels in the one or more first images, determining at least one correction parameter associated with the pixel and determining, based on the initial input function and the at least one correction parameter, a target input function associated with the pixel. The method may further include generating one or more target image sequences based at least in part on a plurality of target input functions associated with the plurality of pixels in the one or more first images. The one or more target image sequences may relate to one or more dynamic parameters associated with the subject, respectively.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 6 is a flowchart illustrating an exemplary process for determining at least one correction parameter for a pixel according to some embodiments of the present disclosure;

FIG. 7 is a flowchart illustrating an exemplary process for generating at least one target image sequence corresponding to at least one second dynamic parameter using an indirect reconstruction algorithm according to some embodiments of the present disclosure; and FIG. 8 is a flowchart illustrating an exemplary process for generating at least one target image sequence corresponding to at least one second dynamic parameter using an indirect reconstruction algorithm according to some embodiments of the present disclosure.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

Figure 2:
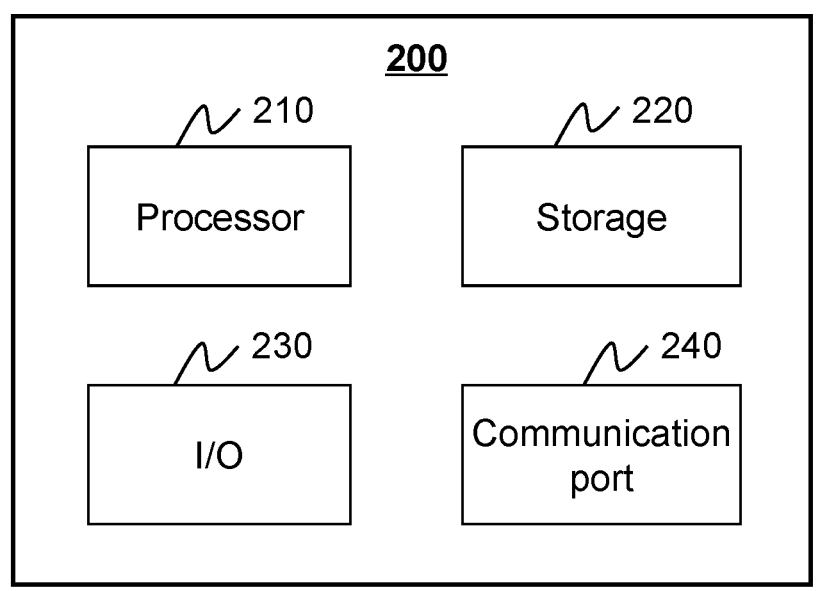
FIG. 2 is a schematic diagram illustrating exemplary hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interruptions. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for an imaging system. In some embodiments, the imaging system may include a single modality imaging system and/or a multi-modality imaging system. The single modality imaging system may include, for example, a PET system, a SPECT system, or the like, or any combination thereof. The multi-modality imaging system may include, for example, a positron emission tomography-X-ray imaging (PET-X-ray) system, a single photon emission computed tomography-magnetic resonance imaging (SPECT-MRI) system, a positron emission tomography-computed tomography (PET-CT) system, a digital subtraction angiography-magnetic resonance imaging (DSA-MRI) system, etc. It should be noted that the imaging system described below is merely provided for illustration purposes, and not intended to limit the scope of the present disclosure.

The present disclosure provides mechanisms (which can include methods, systems, computer-readable mediums, etc.) for reconstructing parametric images. As used herein, a parametric image, also referred to as a target image sequence, corresponds to a dynamic parameter associated with an organ, a tissue, or a part thereof. A first image sequence may be determined based on at least a portion of scan data (e.g., scan data of an early stage of a full scan) of the subject. To more accurately determine an input function that relates to a concentration of an agent in blood vessels (e.g., in the blood or the plasma) of a subject, at least one correction parameter may be determined for each of a plurality of pixels (or voxels) in one or more first images (e.g., standardized uptake value (SUV) images) in the first image sequence. For example, the at least one correction parameter may include a first parameter associated with a dispersion effect and/or a second parameter associated with a time delay effect. For instance, a relationship among a set of first dynamic parameters associated with the subject, an initial input function, the at least one correction parameter, and an output function may be determined using a first kinetic model (e.g., a one-tissue compartment model). The output function may indicate a concentration of the agent in at least a part of a tissue of the subject. The at least one correction parameter may be estimated based on the relationship, the initial input function, and the output function using an iterative algorithm, such as a Maximum Likelihood Estimation (MLE) algorithm. In this manner, a corrected input function (also referred to as a target input function) may be determined for each of the plurality of pixels. One or more parametric images may be more accurately generated based at least in part on the plurality of corrected input functions associated with the plurality of pixels. The correction of input functions on the pixel level may also obviate the need to identify various organs or tissues in an image (sometimes performed manually) for the purposes of performing an organ-based or tissue-based correction of input functions, which in turn avoids the need to acquire an image of at least certain accuracy and perform image segmentation on the image. Accordingly, the systems and methods disclosed herein may improve accuracy of the input functions and the resulting parametric images and achieve automation of the processes of input function correction and/or image reconstruction.

Figure 1:
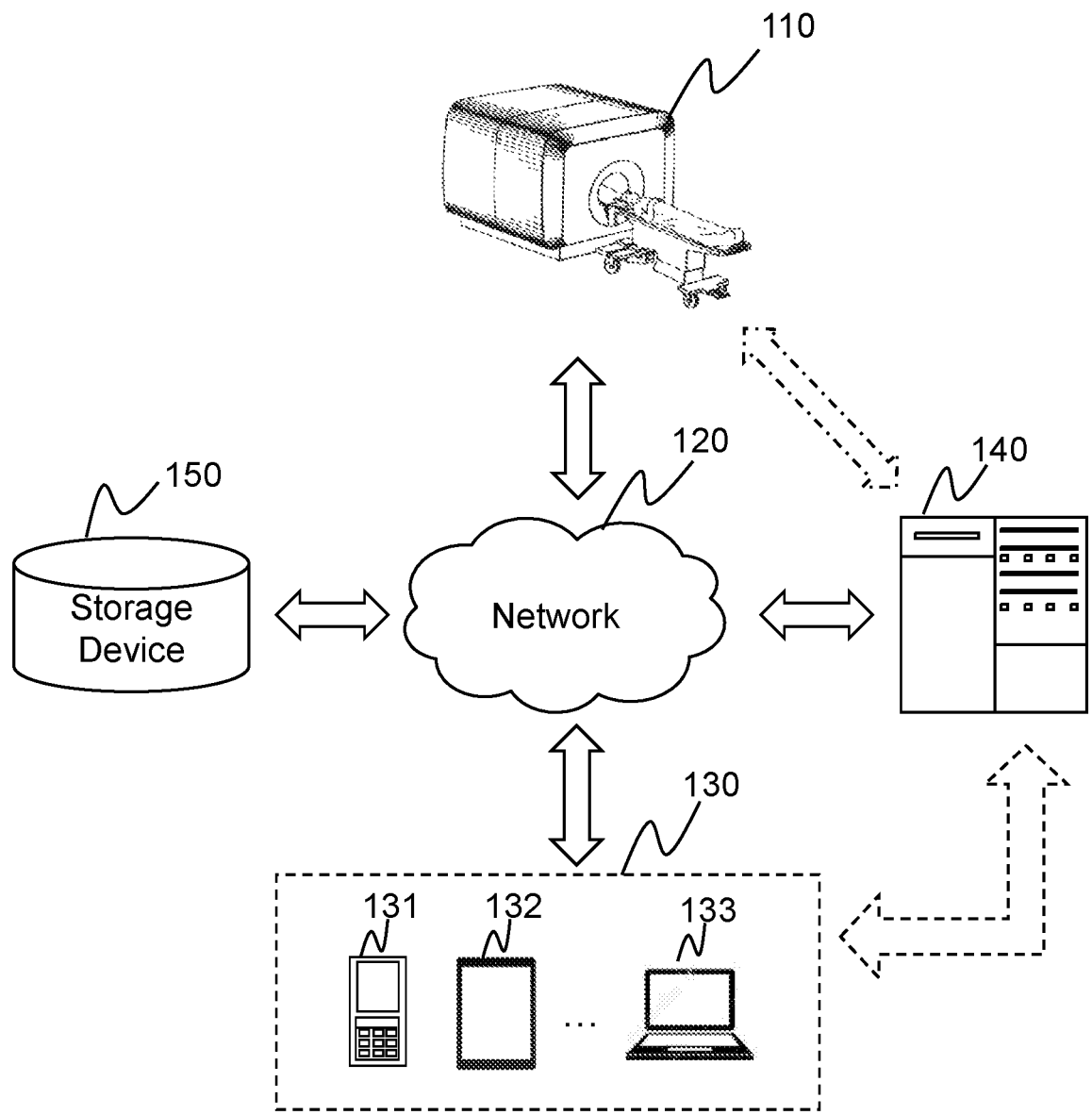
FIG. 1 is a schematic diagram illustrating an exemplary imaging system according to some embodiments of the present disclosure.

FIG. 1 is a schematic diagram illustrating an exemplary imaging system 100 according to some embodiments of the present disclosure. As shown, the imaging system 100 may include a scanner 110, a network 120, one or more terminals 130, a processing device 140, and a storage device 150. In some embodiments, the scanner 110, the terminal(s) 130, the processing device 140, and/or the storage device 150 may be connected to and/or communicate with each other via a wireless connection (e.g., the network 120), a wired connection, or a combination thereof. The connection between the components of the imaging system 100 may be variable. Merely by way of example, the scanner 110 may be connected to the processing device 140 through the network 120, as illustrated in FIG. 1. As another example, the scanner 110 may be connected to the processing device 140 directly. As a further example, the storage device 150 may be connected to the processing device 140 through the network 120, as illustrated in FIG. 1, or connected to the processing device 140 directly. As still a further example, a terminal 130 may be connected to the processing device 140 through the network 120, as illustrated in FIG. 1, or connected to the processing device 140 directly.

The scanner 110 may generate or provide image data via scanning a subject (e.g., a patient) disposed on a scanning table of the scanner 110. In some embodiments, the scanner 110 may be a Positron Emission Tomography (PET) device, a Single Photon Emission Computed Tomography (SPECT) device, a Positron Emission Tomography-Computed Tomography (PET-CT) device, a Single Photon Emission Computed Tomography-Magnetic Resonance Imaging (SPECT-MRI) system, etc. In some embodiments, the subject may include a body, a substance, an object, or the like, or a combination thereof. In some embodiments, the subject may include a specific portion of a body, such as a head, a thorax, an abdomen, or the like, or a combination thereof. In some embodiments, the subject may include a specific organ or region of interest, such as an esophagus, a trachea, a bronchus, a stomach, a gallbladder, a small intestine, a colon, a bladder, a ureter, a uterus, a fallopian tube, etc.

In some embodiments, the scanner 110 may include a gantry, a detector, an electronics module, a table, and/or other components not shown, for example, a cooling assembly. The scanner 110 may scan a subject and obtain information related to the subject. The gantry may support components (e.g., the detector) necessary to produce and detect radiation events to generate an image. The table may position a subject in a detection region. The detector may detect radiation events (e.g., gamma photons) emitted from the detection region. In some embodiments, the detector may include a plurality of detector units. The detector units may be implemented in a suitable manner, for example, a ring, a rectangle, or an array. In some embodiments, the detector unit may include one or more crystal elements and/or one or more photomultiplier tubes (PMT) (not shown). In some embodiments, a PMT as employed in the present disclosure may be a single-channel PMT or a multi-channel PMT. The electronics module may collect and/or process electrical signals (e.g., scintillation pulses) generated by the detector. The electronics module may include an adder, a multiplier, a subtracter, an amplifier, a drive circuit, a differential circuit, a integral circuit, a counter, a filter, an analog-to-digital converter (ADC), a lower limit detection (LLD) circuit, a constant fraction discriminator (CFD) circuit, a time-todigital converter (TDC), a coincidence circuit, or the like, or any combination thereof. In some embodiments, the detected radiation events may be stored or archived in a storage (e.g., the storage device 150), displayed on a display (e.g., a screen on a computing device), or transferred to a connected device (e.g., an external database). In some embodiments, a user may control the scanner 110 via a computing device.

In some embodiments, the scanner 110 may be integrated with one or more other devices that may facilitate the scanning of the subject, such as, an image-recording device. The image-recording device may be configured to take various types of images related to the subject. For example, the image-recording device may be a two-dimensional (2D) camera that takes pictures of the exterior or outline of the subject. As another example, the image-recording device may be a 3D scanner (e.g., a laser scanner, an infrared scanner, a 3D CMOS sensor) that records the spatial representation of the subject.

The network 120 may include any suitable network that can facilitate the exchange of information and/or data for the imaging system 100. In some embodiments, one or more components of the imaging system 100 (e.g., the scanner 110, the processing device 140, the storage device 150, the terminal(s) 130) may communicate information and/or data with one or more other components of the imaging system 100 via the network 120. For example, the processing device 140 may obtain image data from the scanner 110 via the network 120. As another example, the processing device 140 may obtain user instruction(s) from the terminal(s) 130 via the network 120. The network 120 may be or include a public network (e.g., the Internet), a private network (e.g., a local area network (LAN)), a wired network, a wireless network (e.g., an 802.11 network, a WIFI™ network), a frame relay network, a virtual private network (VPN), a satellite network, a telephone network, routers, hubs, switches, server computers, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a BLUETOOTH™ network, a ZIGBEE™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

The terminal(s) 130 may be connected to and/or communicate with the scanner 110, the processing device 140, and/or the storage device 150. For example, the terminal(s) 130 may obtain a processed image from the processing device 140. As another example, the terminal(s) 130 may obtain image data acquired via the scanner 110 and transmit the image data to the processing device 140 to be processed. In some embodiments, the terminal(s) 130 may include a mobile device 131, a tablet computer 132, a laptop computer 133, or the like, or any combination thereof. For example, the mobile device 131 may include a mobile phone, a personal digital assistance (PDA), a gaming device, a navigation device, a point of sale (POS) device, a laptop, a tablet computer, a desktop, or the like, or any combination thereof. In some embodiments, the terminal(s) 130 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing device 140 via, for example, a bus, for further processing. Other types of input devices may include a cursor control device, such as a mouse, a trackball, or cursor direction keys, etc. The output device may include a display, a speaker, a printer, or the like, or a combination thereof. In some embodiments, the terminal(s) 130 may be part of the processing device 140.

In some embodiments, the terminal(s) 130 may send and/or receive information for parametric image reconstruction to the processing device 140 via a user interface. The user interface may be in the form of an application for parametric image reconstruction implemented on the terminal(s) 130. The user interface implemented on the terminal (s) 130 may be configured to facilitate communication between a user and the processing device 130. In some embodiments, a user may input a request for parametric image reconstruction via the user interface implemented on the terminal(s) 130. The terminal(s) 130 may send the request for parametric image reconstruction to the processing device 140 for reconstructing a parametric image based on a plurality of target input functions as described elsewhere in the present disclosure (e.g., FIG. 5 and the descriptions thereof). In some embodiments, the user may input and/or adjust parameters (e.g., weights) of the target machine learning model via the user interface.

The storage device 150 may store data, instructions, and/or any other information. In some embodiments, the storage device 150 may store data obtained from the processing device 140, the terminal(s) 130, and/or the scanner 110. For example, the storage device 150 may store scan data obtained from the scanner 110. As another example, the storage device 150 may store one or more reconstructed parametric images (i.e., target image sequences). In some embodiments, the storage device 150 may store data and/or instructions that the processing device 140 may execute or use to perform exemplary methods described in the present disclosure. In some embodiments, the storage device 150 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform as described elsewhere in the disclosure.

In some embodiments, the storage device 150 may be connected to the network 120 to communicate with one or more other components of the imaging system 100 (e.g., the processing device 140, the terminal(s) 130). One or more components of the imaging system 100 may access the data or instructions stored in the storage device 150 via the network 120. In some embodiments, the storage device 150 may be part of the processing device 140.

In some embodiments, a three-dimensional coordinate system may be used in the imaging system 100 as illustrated in FIG. 1. A first axis may be parallel to the lateral direction of the scanning table 114 (e.g., the X direction perpendicular to and pointing out of the paper as shown in FIG. 1). A second axis may be parallel to the longitudinal direction of the scanning table 114 (e.g., the Z direction as shown in FIG. 1). A third axis may be along a vertical direction of the scanning table 114 (e.g., the Y direction as shown in FIG. 1). The origin of the three-dimensional coordinate system may be any point in the space. The origin of the three-dimensional coordinate system may be determined by an operator. The origin of the three-dimensional coordinate system may be determined by the imaging system 100.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage device 150 may be a data storage including cloud computing platforms, such as public cloud, private cloud, community, and hybrid clouds, etc. However, those variations and modifications do not depart the scope of the present disclosure.

FIG. 2 is a schematic diagram illustrating exemplary hardware and/or software components of an exemplary computing device 200 on which the processing device 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may process image data obtained from the scanner 110, the terminals 130, the storage device 150, and/or any other component of the imaging system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the scanner 110, the terminals 130, the storage device 150, and/or any other component of the imaging system 100. In some embodiments, the storage 220 may include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 140 for determining the position of a target region of a subject (e.g., a target portion of a patient).

The I/O 230 may input and/or output signals, data, information, etc. In some embodiments, the I/O 230 may enable user interaction with the processing device 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing device 140 and the scanner 110, the terminals 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a BLUETOOTH™ link, a WIFI™ link, a WIMAX™ link, a WLAN link, a ZIGBEE™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
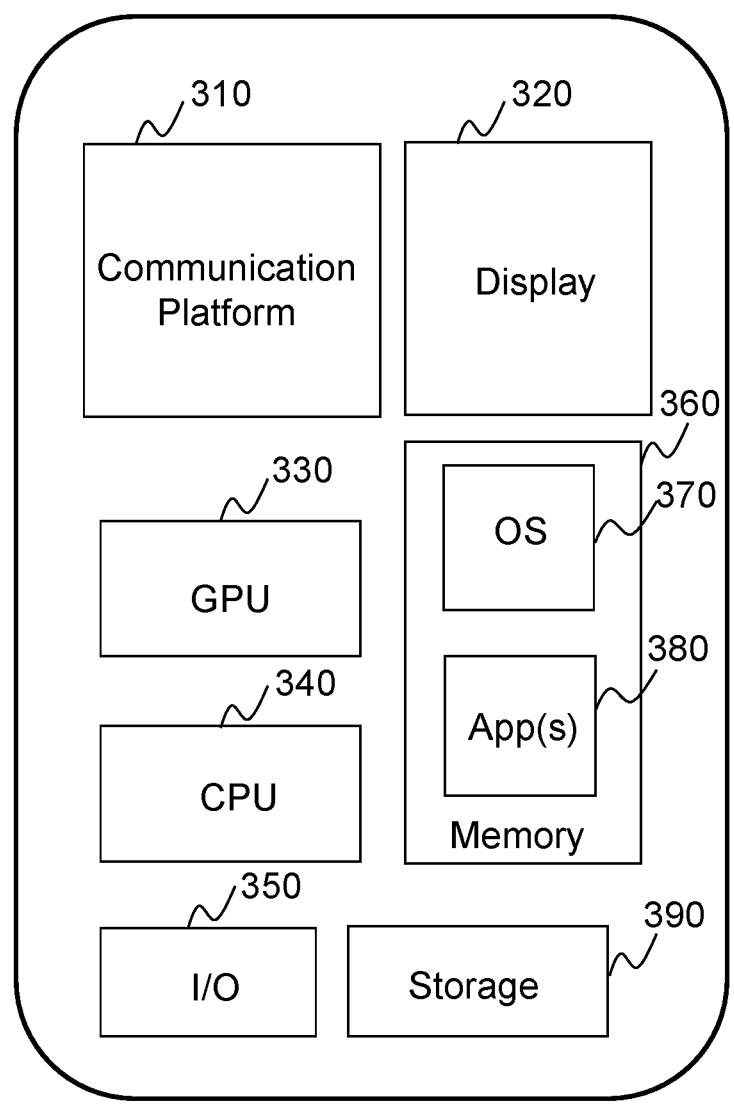
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device 300 on which the terminals 130 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., IOS™, ANDROID™, WINDOWS PHONE™) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the imaging system 100 via the network 120.

To implement various modules, units, and functionalities described in the present disclosure, computer hardware platforms may be used as the hardware platform(s) for one or more of the elements described herein. A computer with user interface elements may be used to implement a personal computer (PC) or any other type of workstation or terminal device. A computer may also act as a server if appropriately programmed.

Figure 4:
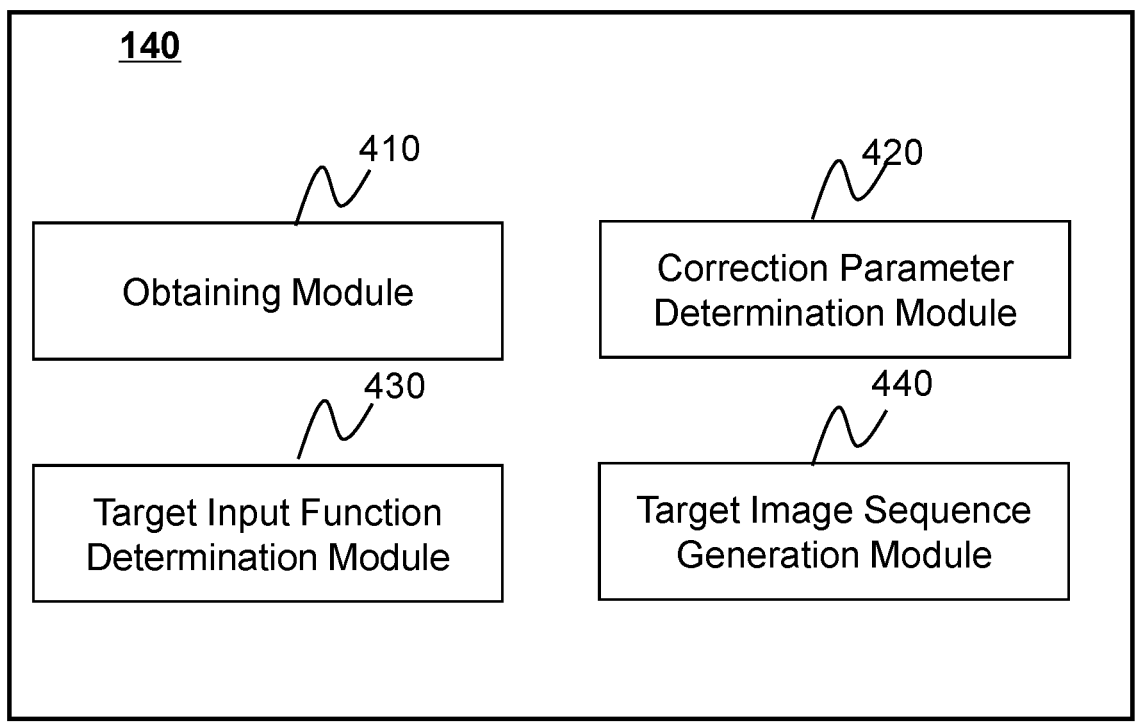
FIG. 4 is a block diagram illustrating an exemplary processing device according to some embodiments of the present disclosure.

FIG. 4 is a block diagram illustrating an exemplary processing device 140 according to some embodiments of the present disclosure. As illustrated in FIG. 4, the processing device 140 may include an obtaining module 410, a correction parameter determination module 420, a target input function determination module 430, and a target image sequence generation module 440. The modules may be hardware circuits of all or part of the processing device 140. The modules may also be implemented as an application or a set of instructions read and executed by the processing device 140. Further, the modules may be any combination of the hardware circuits and the application/instructions. For example, the modules may be part of the processing device 140 when the processing device 140 is executing the application/set of instructions.

The obtaining module 410 may obtain data related to image processing. In some embodiments, the obtaining module 410 may obtain a first image sequence of a subject. An agent may be administered to the subject before a scan (e.g., a PET scan, a SPECT scan) is performed on a region of interest (ROI) of the subject. For example, the agent may be a radioactive tracer. In some embodiments, the radioactive tracer may include a substrate of metabolism at the ROI of the subject (e.g., an animal or a patient). The distribution of the radioactive tracer may indicate information of biological activities in the ROI. In some embodiments, the one or more first images may be generated based on a first portion of the scan data corresponding to an early stage of the scan (e.g., within the first 90 seconds, 150 seconds, or 180 seconds of the scan). In some embodiments, the obtaining module 410 may obtain an initial input function that relates to a concentration of the agent in blood vessels of the subject with respect to time. The initial input function may be a blood TAC that indicates the TAC of the agent in the whole blood, or a plasma TAC that indicates the TAC of the agent in the plasma. In some embodiments, the obtaining module 410 may obtain a second image sequence that is generated based on a second portion of the scan data. The second image sequence may include one or more second images. In some embodiments, the second portion of the scan data may correspond to the rest of the scan after the early stage. In some embodiments, the second portion of the scan data may at least partially overlap the first portion of the scan data. For instance, the second portion of the scan data may correspond to the whole scan.

The correction parameter determination module 420 may determine at least one correction parameter for each of the plurality of pixels in the first image sequence. In some embodiments, the input function associated with the agent at various positions of the body of the subject may vary, for example, due to a dispersion effect, a time delay effect, etc. The at least one correction parameter may include a first parameter associated with the dispersion effect and/or a second parameter associated with the time delay effect. The correction parameter determination module 420 may determine, based on the one or more first images in the first image sequence, an output function that relates to a concentration of the agent in at least a part of a tissue of the subject. The correction parameter determination module 420 may further determine, using a first kinetic model, a relationship among a set of first dynamic parameters associated with the subject, the initial input function, the at least one correction parameter, and the output function. The set of first dynamic parameters may be related to the first kinetic model. The first kinetic model may describe kinetics relating to the agent after the agent is administered to the subject. The first kinetic model may be a relatively simple kinetic model, such as a one-tissue compartment model. For instance, the set of first dynamic parameters may include a transportation rate of the agent from plasma to tissue, a transport rate of the agent from the tissue to the plasma, a concentration of plasma in the tissue, or the like, or any combination thereof. The correction parameter determination module 420 may further determine the at least one correction parameter based on the relationship, the initial input function, and the output function.

The target input function determination module 430 may determine a target input function for each of the plurality of pixels in the first image sequence. Since the target input function is determined for each of the plurality of pixels in the one or more first images, the target input function may be more accurate than the single initial input function applied to each of the plurality of pixels in the one or more first images.

The target image sequence generation module 440 may generate one or more target image sequences corresponding to one or more dynamic parameters. In some embodiments, the target image sequence generation module 440 may generate at least one target image sequence corresponding to at least one of the set of first dynamic parameters (e.g., the transportation rate of the agent from plasma to tissue, the concentration of plasma in the tissue) based on the relationship among the set of first dynamic parameters, the initial input function, the at least one correction parameter, and the output function. In some embodiments, the first parameter and/or the second parameter may also be considered as dynamic parameter(s). The target image sequence generation module 440 may generate the target image sequence(s) corresponding to the first parameter and/or the second parameter. In some embodiments, the target image sequence generation module 440 may further generate at least one target image sequence corresponding to at least one second dynamic parameter. In some embodiments, at least one of the one or more second dynamic parameters may be different from the set of first dynamic parameters. For example, the second dynamic parameters may include dynamic parameters associated with a second kinetic model. Merely by way of example, the second kinetic model may be a two-tissue compartment model.

The target image sequence generation module 440 may reconstruct the at least one target image sequence corresponding to the at least one second dynamic parameter using an indirect reconstruction algorithm or a direct reconstruction algorithm. Using the indirect reconstruction algorithm, the target image sequence generation module 440 may obtain a second image sequence generated based on a second portion of the scan data. The second image sequence may include one or more second images that present the uptake of the agent in the ROI. In some embodiments, the second portion of the scan data may correspond to the rest of the scan after the early stage. In some embodiments, the second portion of the scan data may at least partially overlap the first portion of the scan data. Then the target image sequence generation module 440 may generate at least one target image sequence corresponding to at least one second dynamic parameter based on a second kinetic model, the second image sequence, and the plurality of target input functions associated with the plurality of pixels in the one or more first images. Using the direct reconstruction algorithm, the target image sequence generation module 440 may determine an estimation function based on a second kinetic model and a projection model. The target image sequence generation module 440 may further determine the at least one second dynamic parameter based on the estimation function and the scan data.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, any module mentioned above may be divided into two or more units. In some embodiments, the processing device 140 may include one or more additional modules. For example, the processing device 140 may further include a control module configured to generate control signals for one or more components in the imaging system 100.

Figure 5:
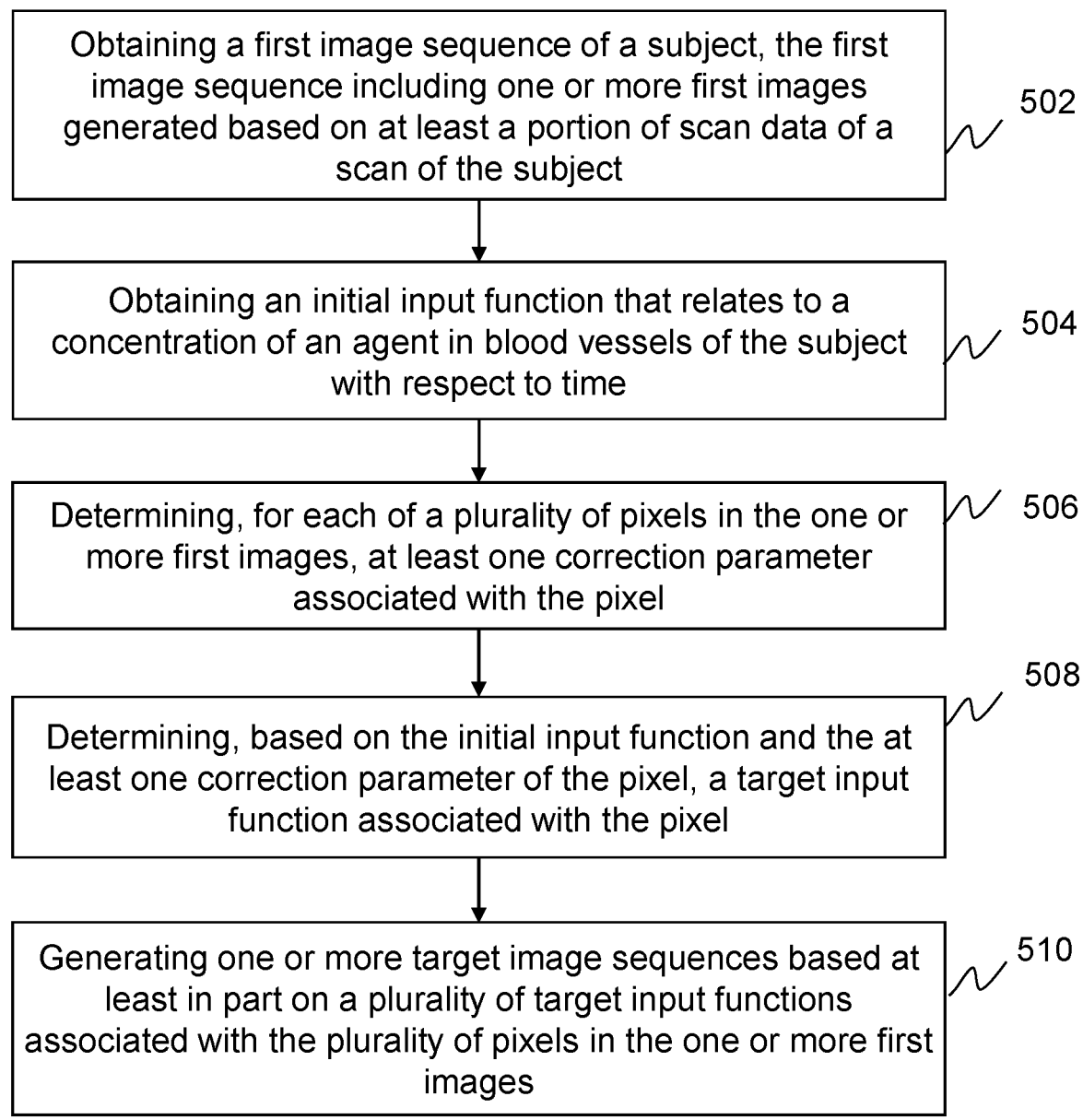
FIG. 5 is a flowchart illustrating an exemplary process for generating at least one target image sequence according to some embodiments of the present disclosure.

FIG. 5 is a flowchart illustrating an exemplary process for generating at least one target image sequence according to some embodiments of the present disclosure. At least a portion of process 500 may be implemented on the computing device 200 as illustrated in FIG. 2 or the mobile device 300 as illustrated in FIG. 3. In some embodiments, one or more operations of the process 500 may be implemented in the imaging system 100 as illustrated in FIG. 1. In some embodiments, one or more operations in the process 500 may be stored in the storage device 150 and/or the storage 220 (e.g., a ROM, a RAM, etc.) as the form of instructions, and invoked and/or executed by the processing device 140, or the processor 210 of the processing device 140. In some embodiments, the instructions may be transmitted to one or more components of the system 100 in the form of electronic current or electrical signals.

In 502, the processing device 140 (e.g., the obtaining module 410) may obtain a first image sequence of a subject. An agent may be administered to the subject before a scan (e.g., a PET scan, a SPECT scan) is performed on a region of interest (ROI) of the subject. For example, the agent may be a radioactive tracer. In some embodiments, the radioactive tracer may include a substrate of metabolism at the ROI of the subject (e.g., an animal or a patient). The distribution of the radioactive tracer may indicate information of biological activities in the ROI. For instance, the radioactive tracer may include [$^{15}$O]H$_2$O, [$^{15}$O]butanol, [$^{11}$C]butanol [$^{18}$F]fluorodeoxyglucose (FDG), [$^{64}$Cu]diacetyl-bis ($^{64}$Cu-ATSM), [$^{18}$F]fluoride, 3'-deoxy-3'-[$^{18}$F]fluorothymidine (FLT), [$^{18}$F]-fluoromisonidazole (FMISO), gallium, thallium, or the like, or the like, or any combination thereof. In some embodiments, the agent may be a therapeutic agent marked with a radioactive isotope, such as $^{15}$O, $^{11}$C, etc. The distribution and therapeutic effect of the therapeutic agent may be estimated based on scan data acquired during the scan.

In some embodiments, the ROI to be scanned may include tissue and/or one or more organs of the subject. For example, the ROI may be a portion of the subject, including the heart, a lung, the liver, the spleen, or the like, or any combination thereof. As another example, the ROI may be the whole body of the subject. The first image sequence may include one or more first images generated based on at least a portion of scan data of the scan of the subject. The one or more first images may present the uptake of the tracer in the ROI. For instance, the one or more first images may include one or more standardized uptake value (SUV) images. In some embodiments, the one or more first images may be generated based on a first portion of the scan data corresponding to an early stage of the scan (e.g., within the first 90 seconds, 150 seconds, or 180 seconds of the scan). Exemplary image reconstruction algorithms for generating the one or more first images may include an iterative algorithm, an analysis algorithm, etc. The iterative algorithm may include a Maximum Likelihood Estimation (MLE) algorithm, an ordered subset expectation maximization (OSEM), a 3D reconstruction algorithm, etc. The analysis algorithm may include a filtered back projection (FBP) algorithm. In some embodiments, the processing device 140 may obtain the first image sequence from a storage device (e.g., the storage device 150).

In 504, the processing device 140 (e.g., the obtaining module 410) may obtain an initial input function that relates to a concentration of the agent in blood vessels of the subject with respect to time. In some embodiments, operation 502 and operation 504 may be performed concurrently or sequentially in any order. In some embodiments, the initial input function may be a time activity curve (TAC) associated with the agent. The initial input function may be a blood TAC that indicates the TAC of the agent in the whole blood, or a plasma TAC that indicates the TAC of the agent in the plasma. In some embodiments, the processing device 140 may designate the plasma TAC or the blood TAC of the agent in a specific organ (e.g., the heart) or tissue as the initial input function. In some embodiments, the blood TAC may be converted to the plasma TAC and then the plasma TAC may be used as the initial input function. In some embodiments, the initial input function may be a dual-input function of the agent, for example, when the ROI includes the liver. As used herein, a dual-input function of a tracer or other agents in an organ or tissue refers to an input function that describes a concentration of the tracer or agent in the organ or tissue that has two entry points for the tracer or agent to enter.

The plasma TAC may be obtained using a gold standard technique (e.g., through the extraction and measurement of arterial blood samples), an arterialization of venous blood technique, a PET blood pool scan technique, a standard input function technique, a fitting function technique, or the like, or a combination thereof. Using the gold standard technique, the arterial blood of the subject may be sampled to measure plasma TAC of the subject. Using the arterialization of venous blood technique, the venous blood of the subject may be sampled to measure plasma TAC of the subject. Using the PET blood pool scan technique, the plasma TAC of the subject may be determined based on the image sequence. For example, the processing device 140 may determine an ROI (e.g., a region associated with the heart or arterial blood) from each of the one or more images in the image sequence. The processing device 140 may identify a blood TAC from the one or more images based on the determined ROI and designate the blood TAC as the plasma TAC. The plasma TAC identified from the image sequence may be also referred to as an image-derived input function. Using the standard input function technique, the plasma TAC of the subject may be determined based on a plurality of plasma TACs of multiple persons (e.g., patients) determined based on the gold standard technique. Further, the plurality of plasma TACs of multiple persons may be normalized and averaged to obtain the plasma TAC of the subject. Using the fitting function technique, the plasma TAC of the subject may be determined by fitting the plurality of plasma TACs of multiple persons. The plasma TAC of the subject determined based on the plurality of plasma TACs of multiple persons may be also referred to as a population-based input function (or standard arterial input function, SAIF). In some embodiments, the plasma TAC of the subject may be determined based on the image sequence and the plurality of plasma TACs of multiple persons. The plasma TAC of the subject determined based on the image-derived input function and the population-based input function may be also referred to as a population-based input function normalized by image (also referred to as PBIFNI). For example, the plasma TAC may be determined by normalizing the population based input function using the image-derived input function. As a further example, the processing device 140 may average the population-based input function and the image-derived input function to obtain the population-based input function normalized by image.

In 506, the processing device 140 (e.g., the correction parameter determination module 420) may determine, for each of a plurality of pixels in the one or more first images, at least one correction parameter associated with the pixel. As used herein, pixels in 2-dimensional images and voxels in 3-dimensional images are both referred to as "pixels." In some embodiments, the input function associated with the agent at various positions of the body of the subject may vary, for example, due to a dispersion effect, a time delay effect, etc. The dispersion effect and the time delay effect may be caused by blood circulation. Specifically, the dispersion effect may be caused by factors including, e.g., the inhomogeneous velocity of the blood in different blood vessels. The time delay effect may be caused by a distance between a blood sampling site and a specific organ or tissue in the ROI. In some embodiments, the at least one correction parameter may include a first parameter associated with the dispersion effect and/or a second parameter associated with the time delay effect.

To determine the at least one correction parameter, the processing device 140 may determine, based on the one or more first images in the first image sequence, an output function that relates to a concentration of the agent in at least a part of a tissue of the subject. The processing device 140 may further determine, using a first kinetic model, a relationship among a set of first dynamic parameters associated with the subject, the initial input function, the at least one correction parameter, and the output function. The set of first dynamic parameters may be related to the first kinetic model. The first kinetic model may describe kinetics relating to the agent after the agent is administered to the subject. The first kinetic model may be a relatively simple kinetic model, such as a one-tissue compartment model. The one-tissue compartment model mainly describes the transport of the agent between the blood/plasma and the tissue. For instance, the set of first dynamic parameters may include a transportation rate of the agent from plasma to tissue, a transport rate of the agent from the tissue to the plasma, a concentration of plasma in the tissue, or the like, or any combination thereof. The processing device 140 may further determine the at least one correction parameter based on the relationship, the initial input function, and the output function. More details regarding the determination of the at least one correction parameter may be found elsewhere in the present disclosure, for example, in the description in connection with FIG. 6.

In 508, the processing device 140 (e.g., the target input function determination module 430) may determine, based on the initial input function and the at least one correction parameter of the pixel, a target input function associated with the pixel. Since the target input function is determined for each of the plurality of pixels in the one or more first images, the target input function may be more accurate than the single initial input function applied to each of the plurality of pixels in the one or more first images. In some embodiments, the target input function for the pixel i may be determined using the following equation (1):

$$C_{input}(t)=k_a e^{-k_a t} \otimes C_p(t-t_d), \qquad (1)$$

where t denotes time that has lapsed since the tracer or agent administration; $C_{input}(t)$ denotes the target input function; $C_p$ denotes the initial input function; $k_a$ denotes the first parameter associated with the dispersion effect; $t_d$ denotes the second parameter associated with the time delay effect; $\otimes$ denotes a convolution operation.

In 510, the processing device 140 (e.g., the target image sequence generation module 440) may generate one or more target image sequences based at least in part on a plurality of target input functions associated with the plurality of pixels in the one or more first images. A target image sequence may include one or more target images presenting the value of a dynamic parameter corresponding to one or more time points during the scan. For example, the one or more target images may be one or more static images corresponding to one or more time points. As another example, the target image sequence may include a dynamic target image, such as a Graphic Interchange Format (GIF) image that presents the change of the dynamic parameter with respect to time. As used herein, the term "dynamic parameter" refers to a physiological parameter associated with the kinetics of the agent after the agent is administered to the subject. The one or more target image sequences may aid the evaluation of the physiology (functionality) and/or anatomy (structure) of an organ and/or tissue in the ROI. For instance, the one or more dynamic parameters may include a transportation rate of the agent from plasma to tissue, a transport rate of the agent from the tissue to the plasma, a concentration of plasma in the tissue, a perfusion rate of the agent, a receptor binding potential of the agent, or the like, or any combination thereof.

In some embodiments, at least one target image sequence corresponding to at least one of the set of first dynamic parameters (e.g., the transportation rate of the agent from plasma to tissue, the concentration of plasma in the tissue) may be generated based on the relationship among the set of first dynamic parameters, the initial input function, the at least one correction parameter, and the output function. In some embodiments, the first parameter and/or the second parameter may also be considered as dynamic parameter(s). The processing device 140 may generate the target image sequence(s) corresponding to the first parameter and/or the second parameter.

In some embodiments, the processing device 140 may further generate at least one target image sequence corresponding to at least one second dynamic parameter. In some embodiments, at least one of the one or more second dynamic parameters may be different from the set of first dynamic parameters. For example, the second dynamic parameters may include dynamic parameters associated with a second kinetic model. The second kinetic model may describe kinetics relating to the agent after the agent is administered to the subject. The second kinetic model may be a compartment model or a non-compartment model, a linear model or a non-linear model, a distributed model or a non-distributed model, or the like, or any combination thereof. Merely by way of example, the second kinetic model may be a two-tissue compartment model. The two-tissue compartment model may describe the transport of the agent between the blood/plasma and the tissue, as well as a phosphorylation process of the agent when the tracer is FDG. The one or more second dynamic parameters for a pixel may include a transportation rate of the agent from plasma to tissue (e.g., at a part of the subject corresponding to the pixel), a transport rate of the agent from the tissue to the plasma, a concentration of plasma in the tissue, a phosphorylation rate of the agent, a dephosphorylation rate of the agent, or the like, or any combination thereof.

The processing device 140 may reconstruct the at least one target image sequence corresponding to the at least one second dynamic parameter using an indirect reconstruction algorithm or a direct reconstruction algorithm. Using the indirect reconstruction algorithm, the processing device 140 may obtain a second image sequence generated based on a second portion of the scan data. The second image sequence may include one or more second images that present the uptake of the agent in the ROI. In some embodiments, the second portion of the scan data may correspond to the rest of the scan after the early stage. In some embodiments, the second portion of the scan data may at least partially overlap the first portion of the scan data. Then the processing device 140 may generate at least one target image sequence corresponding to at least one second dynamic parameter based on a second kinetic model, the second image sequence, and the plurality of target input functions associated with the plurality of pixels in the one or more first images. More details regarding an exemplary indirect reconstruction algorithm may be found elsewhere in the present disclosure, for example, in the description of FIG. 7. Using the direct reconstruction algorithm, the processing device 140 may determine an estimation function based on a second kinetic model and a projection model. The processing device 140 may further determine the at least one second dynamic parameter based on the estimation function and the scan data. More details regarding an exemplary direct reconstruction algorithm may be found elsewhere in the present disclosure, for example, in the description of FIG. 8.

It should be noted that the above description regarding the process 500 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

FIG. 6 is a flowchart illustrating an exemplary process for determining at least one correction parameter for a pixel according to some embodiments of the present disclosure. At least a portion of process 600 may be implemented on the computing device 200 as illustrated in FIG. 2 or the mobile device 300 as illustrated in FIG. 3. In some embodiments, one or more operations of the process 600 may be implemented in the imaging system 100 as illustrated in FIG. 1. In some embodiments, one or more operations in the process 600 may be stored in the storage device 150 and/or the storage 220 (e.g., a ROM, a RAM, etc.) as the form of instructions, and invoked and/or executed by the processing device 140, or the processor 210 of the processing device 140. In some embodiments, the instructions may be transmitted one or more components of the system 100 in the form of electronic current or electrical signals.

In 602, the processing device 140 (e.g., the correction parameter determination module 420) may determine, based on the one or more first images in the first image sequence, an output function that relates to a concentration of the agent in at least a part of a tissue of the subject. For example, the agent may be FDG. The output function may indicate a total concentration of unphosphorylated FDG and phosphorylated FDG in the tissue. In some embodiments, the processing device 140 may determine an output function for each of the plurality of pixels in the one or more first images.

In 604, the processing device 140 (e.g., the correction parameter determination module 420) may determine, using a first kinetic model, a relationship among the set of first dynamic parameters associated with the subject, the initial input function, the at least one correction parameter, and the output function. In some embodiments, the first kinetic model may be a relatively simple kinetic model, such as a one-tissue compartment model. The set of first dynamic parameters may relate to the first kinetic model. In some embodiments, the processing device 140 may independently determine the first parameter associated with the dispersion effect and the second parameter associated with the time delay effect. Merely by way of example, the relationship between the set of first dynamic parameters may be presented using the following equation (2):

$$C(t)=(1-v_b)C_1(t)+v_bC_i(t)=K_1e^{-k_2t}\otimes C_i(t)+v_bC_i(t), \quad (2)$$

where C(t) denotes the output function determined based on the one or more first images; $C_1(t)$ denotes the TAC of the agent in the first compartment of the subject (the amount of tracer(s) transported to the tissue from the plasma); $C_i(t)$ denotes the TAC of the agent in the blood or the plasma of the subject (i.e., the input function with delay and dispersion effect); $K_1$ denotes the transportation rate of the agent from plasma/blood to tissue; $k_2$ denotes the transport rate of the agent from the tissue to the plasma/blood; and $v_b$ denotes the concentration of plasma in the tissue. In combination with equation (1), $C_1(t)$ may be presented using the following equation (3):

$$C_1(t) = K_1(e^{-k_2 t}) \otimes C_i(t) = \int_0^t \int_0^\gamma K_1 k_a (e^{-k_2(t-\gamma)})(e^{-k_a(\gamma-\tau)}) C_p(\tau) d\tau d\gamma, \quad (3)$$

where $k_a$ denotes the first parameter; $\gamma$ and $\tau$ are dummy variables for integration. In combination with equation (3), the relationship may be presented using the following equation (4):

$$C(t) = (1-v_b)K_1 k_a \int_0^t \int_0^\gamma K_1 k_a (e^{-k_2(t-\gamma)})(e^{-k_a(\gamma-\tau)}) C_p(\tau) d\tau d\gamma + \quad (4)$$
$$v_b k_a e^{-k_a t} \otimes C_p(t).$$

In some embodiments, equation (4) may be directly used for estimating $k_a$ based on the initial input function and the output function.

In 606, the processing device 140 (e.g., the correction parameter determination module 420) may determine, the at least one correction parameter based on the relationship, the initial input function, and the output function. In some embodiments, $C_1(t)$ may be presented in a simpler way using the following equation (5):

$$C_1(t) = K_1(e^{-k_2 t}) \otimes C_i(t) = \quad (5)$$
$$\int_0^t \int_0^\gamma K_1 k_a \exp(-k_2 t + k_2 \gamma - k_a \gamma + k_a \tau) C_p(\tau) d\tau d\gamma =$$
$$\int_0^t K_1 k_a C_p(\tau) \exp(-k_2 t + k_a \tau) \int_\tau^t \exp(-(k_a - k_2)\gamma) d\gamma d\tau =$$
$$\int_0^t \frac{K_1 k_a}{(k_a - k_2)} C_p(\tau) \exp(-k_2(t-\tau)) d\tau -$$
$$\int_0^t \frac{K_1 k_a}{(k_a - k_2)} C_p(\tau) \exp(-k_a(t-\tau)) d\tau =$$
$$\frac{K_1 k_a}{(k_a - k_2)} e^{-k_2 t} \otimes C_p(\tau) - \frac{K_1 k_a}{(k_a - k_2)} e^{-k_a t} \otimes C_p(\tau).$$

In combination with equation (5), the relationship may be presented using the following equation (6):

$$C(t) = (1-v_b)C_1(t) + v_b C_i(t) = \quad (6)$$
$$\frac{(1-v_b)K_1 k_a}{(k_a - k_2)} e^{-k_2 t} \otimes C_p(\tau) + \left(-\frac{(1-v_b)K_1 k_a}{(k_a - k_2)} + v_b k_a\right)$$
$$e^{-k_a t} \otimes C_p(\tau) = K_1'(e^{-k_2 t}) \otimes C_p(t) + v_b' e^{-k_a t} \otimes C_p(t),$$
where $$\frac{(1-v_b)K_1 k_a}{(k_a - k_2)} = K_1', \quad (7)$$

and $$v_b k_a - \frac{(1-v_b)K_1 k_a}{(k_a - k_2)} = v_b'. \quad (8)$$

Similarly, the second parameter associated with the time delay effect may be presented using the following equation (9):

$$C(t) = K_1'(e^{-k_2 t}) \otimes C_p(t-t_d) + v_b' e^{-k_a t} \otimes C_p(t-t_d). \quad (9)$$

In some embodiments, the processing device 140 may determine the first parameter and the second parameter based on a preset condition. The preset condition may be associated with the physiological properties of the subject. For instance, the preset condition may be:

$$\begin{cases} k_a > k_2 \\ K_1' > 0 \end{cases}.$$

The first parameter and the second parameter may be estimated using an iterative algorithm. Exemplary iterative algorithms may include an MLE algorithm, an OSEM algorithm, a Maximum Posterior Probability (MAP) algorithm, a Weighted Least Square (WLS) algorithm, or the like, or any combination thereof. Merely by way of example, assuming that the parameters satisfy the Gaussian distribution, the first parameter and the second parameter may be estimated using the least square algorithm with the following equation (10):

$$(k_a, t_d) = \operatorname*{argmin}_{K_1', k_2, v_b', k_a, t_d} \quad (10)$$
$$\int \left( C(t) - \left( K_1'^{(e^{-k_2 t})} \otimes C_p(t-t_d) + v_b' e^{-k_a t} \otimes C_p(t-t_d) \right) \right)^2 dt.$$

After the dynamic parameters $k_a$, $t_d$, $K_1'$, $v_b'$, and $k_2$ are estimated, $K_1$ and $v_b$ may be determined accordingly. In some embodiments, one or more target image sequences corresponding to at least one of the dynamic parameters $k_a$, $t_d$, $K_1'$, $v_b'$, $k_2$, $K_1$ and $v_b$ may be generated.

It should be noted that the above description regarding the process 600 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

FIG. 7 is a flowchart illustrating an exemplary process for generating at least one target image sequence corresponding to at least one second dynamic parameter using an indirect reconstruction algorithm according to some embodiments of the present disclosure. At least a portion of process 700 may be implemented on the computing device 200 as illustrated in FIG. 2 or the mobile device 300 as illustrated in FIG. 3. In some embodiments, one or more operations of the process 700 may be implemented in the imaging system 100 as illustrated in FIG. 1. In some embodiments, one or more operations in the process 700 may be stored in the storage device 150 and/or the storage 220 (e.g., a ROM, a RAM, etc.) as the form of instructions, and invoked and/or executed by the processing device 140, or the processor 210 of the processing device 140. In some embodiments, the instructions may be transmitted to one or more components of one or more components of the system 100 in the form of electronic current or electrical signals.

In 702, the processing device 140 (e.g., the obtaining module 410) may obtain a second image sequence generated based on a second portion of the scan data, the second image sequence including one or more second images. In some embodiments, the second portion of the scan data may correspond to the rest of the scan after the early stage. In some embodiments, the second portion of the scan data may at least partially overlap the first portion of the scan data. For instance, the second portion of the scan data may correspond to the whole scan. The second image sequence may include one or more second images that present the uptake of the agent in the ROI. The one or more second images may be reconstructed in a similar manner as the one or more first images as described in operation 502.

In 704, the processing device 140 (e.g., the target image sequence generation module 440) may generate at least one target image sequence corresponding to at least one second dynamic parameter based on the second kinetic model, the second image sequence, and the plurality of target input functions associated with the plurality of pixels in the one or more first images. In some embodiments, the one or more second dynamic parameters may be different from the set of first dynamic parameters. For example, the second dynamic parameters may include dynamic parameters associated with a second kinetic model, while the first dynamic parameters may include dynamic parameters associated with a first kinetic model. The first kinetic model and the second kinetic model both describe the kinetics relating to the agent after the agent is administered to the subject. In some embodiments, the first kinetic model may be simpler than the second kinetic model. Merely by way of example, the second kinetic model may be a two-tissue compartment model and the agent may be FDG. For each of the plurality of pixels in the one or more second images, a relationship between the input function, the output function, and one or more second dynamic parameters may be presented based on the target input function using the following equation (11):

$$C(t)=(1-v_b)(C_1(t)+C_2(t))+v_b C_{input}(t), \quad (11)$$

where $C_1(t)$ denotes the concentration of unphosphorylated FDG in the tissue; $C_2(t)$ denotes the concentration of phosphorylated FDG in the tissue, where $$\begin{cases} C_1(t) = \dfrac{K_1}{\alpha_2 - \alpha_1}((k_4 - \alpha_1)e^{-\alpha_1 t} + (\alpha_2 - k_4)e^{-\alpha_2 t}) \otimes C_{if}(t) \\ C_2(t) = \dfrac{K_1 k_3}{\alpha_2 - \alpha_1}(e^{-\alpha_1 t} - e^{-\alpha_2 t}) \otimes C_{if}(t) \end{cases}, \quad (12)$$

where $$\begin{cases} \alpha_1 = \dfrac{k_2 + k_3 + k_4 - \sqrt{(k_2 + k_3 + k_4)^2 - 4k_2 k_4}}{2} \\ \alpha_2 = \dfrac{k_2 + k_3 + k_4 + \sqrt{(k_2 + k_3 + k_4)^2 - 4k_2 k_4}}{2} \end{cases}, \quad (13)$$

where $k_3$ denotes the phosphorylation rate of the agent; $k_4$ denotes a dephosphorylation rate. In some embodiments, assuming that the dynamic parameters satisfy the Gaussian distribution, $k_3$ and $k_4$ may be determined using an MLE algorithm with the following equation (14):

$$(K_1, k_2, k_3, k_4, v_b) = \underset{K_1,k_2,k_3,k_4,v_b}{\operatorname{argmin}} \int (C(t) - ((1 - v_b)(C_1(t) + C_2(t)) + v_b C_{input}(t)))^2 dt. \quad (14)$$

In some embodiments, the values of $K_1$, $k_2$, and $v_b$ may be determined as described in operation 606. In some embodiments, the values of $K_1$, $k_2$, and $v_b$ may be re-determined using equation (14). In some embodiments, one or more target image sequences corresponding to the at least one second parameter may be generated. The one or more target image sequences may be used for the evaluation of the physiology (functionality) and/or anatomy (structure) of the ROI.

It should be noted that the above description regarding the process 600 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, the target image sequences generated based on the parameters determined in the process 600 may be adequate for diagnosis use and the process 700 may be omitted.

FIG. 8 is a flowchart illustrating an exemplary process for generating at least one target image sequence corresponding to at least one second dynamic parameter using an indirect reconstruction algorithm according to some embodiments of the present disclosure. At least a portion of process 800 may be implemented on the computing device 200 as illustrated in FIG. 2 or the mobile device 300 as illustrated in FIG. 3. In some embodiments, one or more operations of the process 800 may be implemented in the imaging system 100 as illustrated in FIG. 1. In some embodiments, one or more operations in the process 800 may be stored in the storage device 150 and/or the storage 220 (e.g., a ROM, a RAM, etc.) as the form of instructions, and invoked and/or executed by the processing device 140, or the processor 210 of the processing device 140. In some embodiments, the instructions may be transmitted to one or more components of one or more components of the system 100 in the form of electronic current or electrical signals.

In 802, the processing device 140 (e.g., the target image sequence generation module 440) may determine an estimation function for determining at least one second dynamic parameter based on a projection model, a second kinetic model, and the scan data. The projection model may be presented using the following equation (15):

$$Y(t)=AHC(t)+S(t)+R(t), \quad (15)$$

where Y(t) denotes the scan data; H denotes a projection matrix; A denotes an attenuation effect; S(t) denotes a dynamic scattering effect; R(t) denotes random events. The estimation function may be determined according to an iterative algorithm, such as an MLE algorithm, an OSEM algorithm, a MAP algorithm, a WLS algorithm. Merely by way of example, the second kinetic model may be a two-tissue compartment model. The estimation function may be presented as the following equation (16) using the MLE algorithm:

$$L(y,\lambda)=\Sigma_{i,t}-\Sigma_j AH_{i,j} C_t(\lambda_j)+y_{i,t}\log(\Sigma_j H_{i,j} C_t(\lambda_j))-\log(y_{i,t}!), \quad (16)$$

where j denotes the pixels; and λ denotes a variable corresponding to one of $K_1$, $k_2$, $k_3$, $k_4$, and $v_b$. t, the time that has lapsed since the tracer or agent administration, may be considered as a discrete variable.

In 804, the processing device 140 (e.g., the target image sequence generation module 440) may determine an iterative equation for determining the at least one second dynamic parameter based on the estimation function. In some embodiments, the impact of λ on the estimation function may be presented by the derivative as follow:

$$\frac{\partial L(y, \lambda)}{\partial \lambda} = \sum_t \frac{\partial L(y, \lambda)}{\partial C_t} \frac{\partial C_t}{\partial \lambda}, \quad (17)$$

where when $$\frac{\partial C_t}{\partial \lambda} > 0,$$

the iterative equation for determining λ may be obtained in a manner similar to a traditional maximum likelihood expectation maximization (MLEM) algorithm. For example, the iterative equation may be presented using the following equation (18):

$$\lambda_j^{n+1} = \frac{\lambda_j^n}{\sum_{i,t} H_{i,j} \frac{\partial C_t}{\partial \lambda}} \sum_{it} \frac{\frac{\partial C_t}{\partial \lambda} y_{i,t} H_{i,j}}{\sum_k H_{i,k} C_t(\lambda_k) + S_t + R_t}. \quad (18)$$

Equation (18) may be used for estimating $K_1$, $k_3$, and $v_b$. In some embodiments, the values of $K_1$, $k_2$, and $v_b$ may be determined as described in operation 606.

In some embodiments, when $$\frac{\partial C_t}{\partial \lambda} < 0,$$

the iterative equation may be presented using the steepest descent algorithm, for example, by the following equation (19):

$$\lambda_j^{n+1} = \lambda_j^n + s \frac{\partial L(y, \lambda)}{\partial \lambda_j}, \quad (19)$$

where s denotes the step size for iterations, and s>0. The impact of λ on the estimation function may be presented by the following equation (20):

$$\frac{\partial L(y, \lambda)}{\partial \lambda_j} = \sum_t -\frac{\partial C_t}{\partial \lambda} \left( \sum_i H_{i,j} - y_{i,t} \frac{H_{i,j}}{\sum_k H_{i,k} C_t(\lambda_k) + S_t + R_t} \right). \quad (20)$$

If the estimated parameter λ is always positive, positive constraint can be added by transforming the additive update equation to a multiplicative update equation. It can be achieved by choosing the appropriate step size s. In some embodiments, s may be presented using the following equation (21):

$$s = \frac{\lambda_j^n}{\sum_t -\frac{\partial C_t}{\partial \lambda} \sum_i \frac{y_i H_{i,j}}{\sum_k \sum_k H_{i,k} C_t(\lambda_k) + S_t + R_t}}. \quad (21)$$

In some embodiments, the iterative equation may be presented using the following equation (22):

$$\lambda_j^{n+1} = \lambda_j^n + s \frac{\partial L(y, \lambda)}{\partial \lambda_j} = \lambda_j^n - \quad (22)$$

$$\frac{\lambda_j^n}{\sum_t -\frac{\partial C_t}{\partial \lambda} \sum_i \frac{y_i H_{i,j}}{\sum_k \sum_k H_{i,k} C_t(\lambda_k) + S_t + R_t}} \sum_t -$$

$$\frac{\partial C_t}{\partial \lambda} \left( \sum_i H_{i,j} - y_{i,t} \frac{H_{i,j}}{\sum_k H_{i,k} C_t(\lambda_k) + S_t + R_t} \right) =$$

$$\frac{\lambda_j^n \sum_{i,t} H_{i,j} \frac{\partial C_t}{\partial \lambda}}{\sum_t \frac{\partial C_t}{\partial \lambda} \sum_i \frac{y_i H_{i,j}}{\sum_k \sum_k H_{i,k} C_t(\lambda_k) + S_t + R_t}}$$

Equation (22) may be used for estimating $k_2$ and $k_4$.

In 806, the processing device 140 (e.g., the target image sequence generation module 440) may generate at least one target image sequence corresponding to the at least one second dynamic parameter by performing an iterative operation based on the iterative equation. In some embodiments, one or more target image sequences corresponding to the at least one second parameter may be generated. The one or more target image sequences may be used for the evaluation of the physiology (functionality) and/or anatomy (structure) of the ROI.

In some embodiments, other indirect or direct reconstruction algorithms may also be adopted to generate the at least one target image sequence corresponding to the at least one second dynamic parameter, which are not limited by the present disclosure. For instance, a nested reconstruction algorithm may be adopted. The processing device 140 may determine, for each of a plurality of pixels in a target image sequence and according to an alternative and iterative process, the output function and the at least one second dynamic parameter. For example, the processing device 140 may determine a first iterative equation for estimating the output function using the projection model (e.g., presented by equation (11)). The processing device 140 may determine a second iterative equation for estimating the at least one second dynamic parameter based on the output function using the second kinetic model. The processing device 140 may determine an initial value for the output function. In some embodiments, the initial value for the output function may be determined using an image reconstruction algorithm for generating an SUV image based on the scan data. In the alternative and iterative process, the processing device 140 may update the at least one second dynamic parameter based on the second iterative equation and the current value of the output function; and the processing device 140 may update the output function based on the current value(s) of the at least one second dynamic parameter. The alternative and iterative process may be performed repeatedly until convergence is reached. The processing device 140 may further generate at least one target image sequence corresponding to the at least one second dynamic parameter based on the value(s) of the at least one second dynamic parameter in the last iteration.

It should be noted that the above description regarding the process 600 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, the target image sequences generated based on the parameters determined in the process 600 may be adequate for diagnosis use and the process 800 may be omitted.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lies in less than all features of a single foregoing disclosed embodiment.

What is claimed is:
1. A system for image reconstruction, comprising:
   at least one non-transitory storage medium including a set of instructions; and
   at least one processor in communication with the at least one non-transitory storage medium, wherein when executing the set of instructions, the at least one processor is configured to cause the system to perform operations including:
   obtaining a first image sequence of a subject, the first image sequence including one or more first images generated based on a first portion of scan data of a scan of the subject;
   obtaining an initial input function that relates to a concentration of an agent in blood vessels of the subject with respect to time, wherein the agent is administered to the subject before the scan;

for each of a plurality of pixels in the one or more first images, determining, using a first kinetic model that includes an iterative algorithm, at least one correction parameter associated with the pixel, wherein the first kinetic model corresponds to a relationship among a set of first dynamic parameters associated with the subject, the initial input function, the at least one correction parameter, and an output function that indicates a concentration of the agent in at least a part of a tissue of the subject; and determining, by correcting the initial input function with the at least one correction parameter, a target input function associated with the pixel; and generating, using a second kinetic model, one or more target image sequences based at least in part on a plurality of target input functions associated with the plurality of pixels in the one or more first images, wherein the one ore more target image sequences respectively correspond to one or more dynamic parameters that include the set of first dynamic parameters and that are associated with kinetics of the agent after the agent is administered to the subject, each of the target image sequence includes one or more target images, and each target image presents a value of a respective dynamic parameter corresponding to a time point during the scan.

2. The system of claim 1, wherein the at least one correction parameter includes at least one of a first parameter associated with a dispersion effect caused by blood circulation, or a second parameter associated with a time delay effect caused by blood circulation.

3. The system of claim 1, wherein the agent includes a radioactive tracer.

4. The system of claim 1, wherein the first kinetic model is a one-tissue compartment model.

5. The system of claim 1, wherein to determine the at least one correction parameter associated with the pixel, the at least one processor is further configured to cause the system to perform operations including:

determining the at least one correction parameter based further on a preset condition associated with one or more physiological properties of the subject.

6. The system of claim 1, wherein to generate the one or more target image sequences, the at least one processor is further configured to cause the system to perform operations including:

generating, based on the relationship among the set of first dynamic parameters, at least one of the one or more target image sequences corresponding to at least one of the set of first dynamic parameters.

7. The system of claim 1, wherein the one or more dynamic parameters include a set of second dynamic parameters, and to generate the one or more target image sequences, the at least one processor is configured to cause the system to perform operations including:

obtaining a second image sequence generated based on a second portion of the scan data, the second image sequence including one or more second images; and generating at least one of the one or more target image sequences corresponding to at least one second dynamic parameter based on the second kinetic model, the second image sequence, and the plurality of target input functions associated with the plurality of pixels in the one or more first images.

8. The system of claim 7, wherein the second portion of the scan data at least partially overlaps the first portion of the scan data.

9. The system of claim 7, wherein the second portion of the scan data include the first portion of the scan data.

10. The system of claim 1, wherein to generate the one or more target image sequences, the at least one processor is configured to cause the system to perform operations including:

generating at least one of the one or more target image sequences corresponding to at least one second dynamic parameter by performing an iterative operation based on a projection model, the second kinetic model, and the scan data.

11. The system of claim 10, wherein the iterative operation includes a maximum likelihood estimation operation.

12. A method for image reconstruction, implemented on a computing device having at least one processor and at least one non-transitory storage medium, the method comprising:

obtaining a first image sequence of a subject, the first image sequence including one or more first images generated based on a first portion of scan data of a scan of the subject;

obtaining an initial input function that relates to a concentration of an agent in blood vessels of the subject with respect to time, wherein the agent is administered to the subject before the scan;

for each of a plurality of pixels in the one or more first images, determining, using a first kinetic model that includes an iterative algorithm, at least one correction parameter associated with the pixel, wherein the first kinetic model corresponds to a relationship among a set of first dynamic parameters associated with the subject, the initial input function, the at least one correction parameter, and an output function that indicates a concentration of the agent in at least a part of a tissue of the subject; and determining, by correcting the initial input function with the at least one correction parameter, a target input function associated with the pixel; and generating, using a second kinetic model, one or more target image sequences based at least in part on a plurality of target input functions associated with the plurality of pixels in the one or more first images, wherein the one ore more target image sequences respectively correspond to one or more dynamic parameters that include the set of first dynamic parameters and that are associated with kinetics of the agent after the agent is administered to the subject, each of the target image sequence includes one or more target images, and each target image presents a value of a respective dynamic parameter corresponding to a time point during the scan.

13. The method of claim 12, wherein the at least one correction parameter includes at least one of a first parameter associated with a dispersion effect caused by blood circulation, or a second parameter associated with a time delay effect caused by blood circulation.

14. The method of claim 12, wherein the agent includes a radioactive tracer.

15. The method of claim 12, wherein the generating one or more target image sequences based at least in part on a plurality of target input functions associated with the plurality of pixels in the one or more first images includes:

generating, based on the relationship among the set of first dynamic parameters, at least one of the one or more target image sequences corresponding to at least one of the set of first dynamic parameters.

16. The method of claim 12, wherein the one or more dynamic parameters include a set of second dynamic parameters, and the generating one or more target image sequences includes:

obtaining a second image sequence generated based on a second portion of the scan data, the second image sequence including one or more second images; and generating at least one of the one or more target image sequences corresponding to at least one second dynamic parameter based on the second kinetic model, the second image sequence, and the plurality of target input functions associated with the plurality of pixels in the one or more first images.

17. The method of claim 12, wherein the generating one or more target image sequences based at least in part on a plurality of target input functions associated with the plurality of pixels in the one or more first images includes:

generating at least one of the one or more target image sequences corresponding to at least one second dynamic parameter by performing an iterative operation based on a projection model, the second kinetic model, and the scan data.

18. A non-transitory computer readable medium, comprising at least one set of instructions for image reconstruction, wherein when executed by at least one processor of a computing device, the at least one set of instructions direct the at least one processor to perform operations including:

obtaining a first image sequence of a subject, the first image sequence including one or more first images generated based on a first portion of scan data of a scan of the subject;

obtaining an initial input function that relates to a concentration of an agent in blood vessels of the subject with respect to time, wherein the agent is administered to the subject before the scan;

for each of a plurality of pixels in the one or more first images, determining, using a first kinetic model that includes an iterative algorithm, at least one correction parameter associated with the pixel, wherein the first kinetic model corresponds a relationship among a set of first dynamic parameters associated with the subject, the initial input function, the at least one correction parameter, and an output function that indicates a concentration of the agent in at least a part of a tissue of the subject; and determining, by correcting the initial input function with the at least one correction parameter, a target input function associated with the pixel; and generating, using a second kinetic model, one or more target image sequences based at least in part on a plurality of target input functions associated with the plurality of pixels in the one or more first images, wherein the one ore more target image sequences respectively correspond to one or more dynamic parameters that include the set of first dynamic parameters and that are associated with kinetics of the agent after the agent is administered to the subject, each of the target image sequence includes one or more target images, and each target image presents a value of a respective dynamic parameter corresponding to a time point during the scan.

* * * * *